US012744051B2

(12) United States Patent
Kim et al.

(10) Patent No.: US 12,744,051 B2
(45) Date of Patent: Sep. 22, 2026

(54) EMOTION MODELING METHOD AND APPARATUS THEREOF

(71) Applicants: Hyundai Motor Company, Seoul (KR); Kia Corporation, Seoul (KR); SEOUL NATIONAL UNIVERSITY R&DB FOUNDATION, Seoul (KR)

(72) Inventors: Ki Chang Kim, Gyeonggi-do (KR); Dong Chul Park, Gyeonggi-do (KR); Myung Hwan Yun, Seoul (KR); Sung Ho Kim, Seoul (KR)

(73) Assignees: Hyundai Motor Company, Seoul (KR); Kia Corporation, Seoul (KR); Seoul National University R&DB Foundation, Seoul (KR)

( * ) Notice: Subject to any disclaimer, the term of this patent is extended or adjusted under 35 U.S.C. 154(b) by 351 days.

(21) Appl. No.: 17/880,353

(22) Filed: Aug. 3, 2022

(65) Prior Publication Data

US 2023/0223039 A1 Jul. 13, 2023

(30) Foreign Application Priority Data

Jan. 7, 2022 (KR) ........................ 10-2022-0002841

(51) Int. Cl.
*G10L 25/63* (2013.01)
*A61B 5/00* (2006.01)
(Continued)

(52) U.S. Cl.
CPC ............ *G10L 25/63* (2013.01); *A61B 5/7264* (2013.01); *G10L 15/16* (2013.01); *G10L 25/30* (2013.01); *A61B 2503/22* (2013.01); *G06F 40/30* (2020.01)

(58) Field of Classification Search
CPC ......... G10L 25/63; G10L 25/30; G10L 15/04; G10L 15/16; G10L 15/22; A61B 2503/22;
(Continued)

(56) References Cited

U.S. PATENT DOCUMENTS 10,960,816 B2 3/2021 Lee et al.
11,449,744 B2 * 9/2022 Chen ...................... G06N 3/044
(Continued)

FOREIGN PATENT DOCUMENTS

JP 5225847 B2 7/2013
KR 10-0743037 B1 7/2007
(Continued)

OTHER PUBLICATIONS

Yang, Yi-Hsuan, et al. "A regression approach to music emotion recognition." IEEE Transactions on audio, speech, and language processing 16.2 (2008): 448-457. (Year: 2008).*
(Continued)

*Primary Examiner* — Hai Phan
*Assistant Examiner* — Nathan Tengbumroong
(74) *Attorney, Agent, or Firm* — Fox Rothschild LLP

(57) ABSTRACT

An emotion modeling method for providing a vehicle sound with regard to an emotion of a user in a vehicle sound and an apparatus thereof are provided. The emotion modeling apparatus receives a sound by a user utterance, determines an emotional attribute based on the sound using an emotion analysis algorithm, derives an instrumental value of a sound concept by analyzing psychosocial consequences of the emotional attribute using an artificial neural network, and generates an emotional model based on the instrumental value of the sound concept.

6 Claims, 5 Drawing Sheets

(51) Int. Cl.
*G06F 40/30* (2020.01)
*G10L 15/16* (2006.01)
*G10L 25/30* (2013.01)

(58) Field of Classification Search
CPC ......... A61B 5/165; A61B 5/18; A61B 5/7264; A61B 5/4803; A61B 5/7267; G06F 40/284; G06F 40/30; G06N 3/04; G06N 20/00
See application file for complete search history.

(56) References Cited

U.S. PATENT DOCUMENTS

| | | | | |
|---|---|---|---|---|
| 2002/0194002 | A1* | 12/2002 | Petrushin | G10L 17/26<br>704/E17.002 |
| 2009/0316862 | A1 | 12/2009 | Sugimoto et al. | |
| 2011/0100199 | A1 | 5/2011 | Sugimoto et al. | |
| 2016/0234595 | A1* | 8/2016 | Goran | H04L 12/2827 |
| 2016/0379047 | A1* | 12/2016 | Natan | G06V 40/171<br>382/201 |
| 2020/0215294 | A1* | 7/2020 | Lee | A61M 21/02 |
| 2020/0324697 | A1 | 10/2020 | Lee et al. | |
| 2021/0170585 | A1* | 6/2021 | Kim | G06N 20/00 |
| 2021/0304787 | A1* | 9/2021 | Verbeke | G10L 25/63 |
| 2021/0356285 | A1* | 11/2021 | Cella | G06V 20/597 |
| 2022/0185178 | A1* | 6/2022 | Sudo | B60K 35/22 |
| 2022/0357912 | A1 | 11/2022 | Kim et al. | |

FOREIGN PATENT DOCUMENTS

| | | | |
|---|---|---|---|
| KR | 10-2017-0014050 | A | 2/2017 |
| KR | 10-2020598 | B1 | 9/2019 |
| KR | 10-2131391 | B1 | 7/2020 |
| KR | 10-2020-0123503 | A | 10/2020 |
| KR | 10-2022-0152829 | A | 11/2022 |

OTHER PUBLICATIONS

Hazarika, Devamanyu et al. “Conversational Memory Network for Emotion Recognition in Dyadic Dialogue Videos.” Proceedings of the conference. Association for Computational Linguistics. North American Chapter. Meeting 2018 (2018): 2122-2132.

* cited by examiner

EMOTION MODELING METHOD AND APPARATUS THEREOF

CROSS-REFERENCE TO RELATED APPLICATION

This application is based on and claims under 35 U.S.C. § 119 (a) the benefit of Korean Patent Application No. 10-2022-0002841, filed in the Korean Intellectual Property Office on Jan. 7, 2022, the entire contents of which are incorporated herein by reference.

TECHNICAL FIELD

Embodiments of the present disclosure relate to an emotion modeling method for modeling an emotion of a user to provide a vehicle sound considering the emotion of the user in a vehicle environment and an apparatus thereof.

DESCRIPTION OF RELATED ART

A healthcare system is a technology of identifying a state of a driver and guiding the driver to receive guidance and alert and perform safe driving in connection with a vehicle system. The healthcare system may collect biometric information, for example, electrocardiogram (ECG), heart rates, movement of the driver, and the like, using sensors to determine the state of the driver. Furthermore, the healthcare system may recognize a facial expression of the driver using its camera to determine an emotional state of the driver.

SUMMARY

Embodiments of the present disclosure have been made to solve the above-mentioned problems occurring in the prior art while advantages achieved by the prior art are maintained intact.

An embodiment of the present disclosure provides an emotion modeling method for modeling a sound emotion of a user based on an utterance of a user to provide a customized vehicle sound with regard to an emotion of the user in a vehicle environment and an apparatus thereof.

The technical problems to be solved by the present disclosure are not limited to the aforementioned problems, and any other technical problems not mentioned herein will be clearly understood from the following description by those skilled in the art to which the present disclosure pertains.

According to an embodiment of the present disclosure, an emotion modeling method may include receiving a sound by a user utterance, determining an emotional attribute based on the sound using an emotion analysis algorithm, deriving an instrumental value of a sound concept by analyzing psychosocial consequences of the emotional attribute using an artificial neural network, and generating an emotional model based on the instrumental value of the sound concept.

The determining of the emotional attribute may include classifying a user emotion included in the sound using an emotion classifier and converting the classified user emotion into a concrete attribute.

The classifying of the user emotion may include classifying the user emotion using a conversational memory network (CMN).

The converting of the classified user emotion into the concrete attribute may include matching a related keyword with the classified user emotion.

The generating of the emotional model may include establishing a criterion of determining borderline data by performing position calculation of conservative and progress and stability and fun by means of the instrumental value of the sound concept and determining an emotion modeling methodology based on the criterion.

The analyzing of the psychosocial consequences may include classifying vehicle environment development needs using at least one of logistic regression (LR), a support vector machine (SVM), and a K-nearest neighbor (KNN) algorithm or reflecting the psychosocial consequences in the classified vehicle environment development needs.

The deriving of the instrumental value of the sound concept may include predicting a vehicle environment function using at least one of multiple linear regression (MLR) or support vector regression (SVR) to derive the instrumental value of the sound concept.

According to another embodiment of the present disclosure, an emotion modeling apparatus may include a detector that detects a sound by a user utterance and a processor that determines an emotional attribute based on the sound using an emotion analysis algorithm, derives an instrumental value of a sound concept by analyzing psychosocial consequences of the emotional attribute using an artificial neural network, and generates an emotional model based on the instrumental value of the sound concept.

The processor may classify a user emotion included in the sound using an emotion classifier and may convert the classified user emotion into a concrete attribute.

The processor may classify the user emotion using a conversational memory network (CMN).

The processor may match a related keyword with the classified user emotion.

The processor may establish a criterion of determining borderline data by performing position calculation of conservative and progress and stability and fun by means of the instrumental value of the sound concept and determines an emotion modeling methodology based on the criterion.

The processor may classify vehicle environment development needs using at least one of logistic regression (LR), a support vector machine (SVM), and a K-nearest neighbor (KNN) algorithm or may reflect the psychosocial consequences in the classified vehicle environment development needs.

The processor may predict a vehicle environment function using at least one of multiple linear regression (MLR) or support vector regression (SVR) to derive the instrumental value of the sound concept.

As discussed, the method and system suitably include use of a controller or processer.

In another aspect, vehicles are provided that comprise an apparatus as disclosed herein.

BRIEF DESCRIPTION OF THE DRAWINGS

The above and other objects, features and advantages of the present disclosure will be more apparent from the following detailed description taken in conjunction with the accompanying drawings.

DETAILED DESCRIPTION

Figure 1:
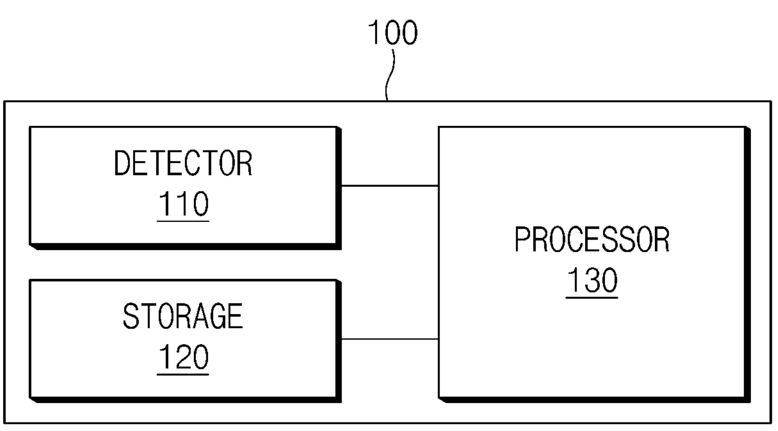
FIG. 1 is a block diagram illustrating a configuration of an emotion modeling apparatus according to embodiments of the present disclosure.

Hereinafter, some embodiments of the present disclosure will be described in detail with reference to the exemplary drawings. In the drawings, the same reference numerals will be used throughout to designate the same or equivalent elements. In addition, a detailed description of well-known features or functions will be ruled out in order not to unnecessarily obscure the gist of the present disclosure.

It is understood that the term "vehicle" or "vehicular" or other similar term as used herein is inclusive of motor vehicles in general such as passenger automobiles including sports utility vehicles (SUV), buses, trucks, various commercial vehicles, watercraft including a variety of boats and ships, aircraft, and the like, and includes hybrid vehicles, electric vehicles, plug-in hybrid electric vehicles, hydrogen-powered vehicles and other alternative fuel vehicles (e.g. fuels derived from resources other than petroleum). As referred to herein, a hybrid vehicle is a vehicle that has two or more sources of power, for example both gasoline-powered and electric-powered vehicles.

The terminology used herein is for the purpose of describing particular embodiments only and is not intended to be limiting of the disclosure. As used herein, the singular forms "a," "an" and "the" are intended to include the plural forms as well, unless the context clearly indicates otherwise. These terms are merely intended to distinguish one component from another component, and the terms do not limit the nature, sequence or order of the constituent components. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Throughout the specification, unless explicitly described to the contrary, the word "comprise" and variations such as "comprises" or "comprising" will be understood to imply the inclusion of stated elements but not the exclusion of any other elements. In addition, the terms "unit", "-er", "-or", and "module" described in the specification mean units for processing at least one function and operation and can be implemented by hardware components or software components and combinations thereof.

Although exemplary embodiment is described as using a plurality of units to perform the exemplary process, it is understood that the exemplary processes may also be performed by one or plurality of modules. Additionally, it is understood that the term controller/control unit refers to a hardware device that includes a memory and a processor and is specifically programmed to execute the processes described herein. The memory is configured to store the modules and the processor is specifically configured to execute said modules to perform one or more processes which are described further below.

Further, the control logic of the present disclosure may be embodied as non-transitory computer readable media on a computer readable medium containing executable program instructions executed by a processor, controller or the like. Examples of computer readable media include, but are not limited to, ROM, RAM, compact disc (CD)-ROMs, magnetic tapes, floppy disks, flash drives, smart cards and optical data storage devices. The computer readable medium can also be distributed in network coupled computer systems so that the computer readable media is stored and executed in a distributed fashion, e.g., by a telematics server or a Controller Area Network (CAN).

In describing the components of the embodiment according to the present disclosure, terms such as first, second, "A", "B", (a), (b), and the like may be used. These terms are only used to distinguish one element from another element, but do not limit the corresponding elements irrespective of the order or priority of the corresponding elements. Furthermore, unless otherwise defined, all terms including technical and scientific terms used herein are to be interpreted as is customary in the art to which this disclosure belongs. Such terms as those defined in a generally used dictionary are to be interpreted as having meanings equal to the contextual meanings in the relevant field of art and are not to be interpreted as having ideal or excessively formal meanings unless clearly defined as having such in the present application.

FIG. 1 is a block diagram illustrating a configuration of an emotion modeling apparatus according to embodiments of the present disclosure.

An emotion modeling apparatus 100 may include a detector 110, a storage 120, and a processor 130.

The detector 110 may detect a sound (or an audio signal) using sensor(s). As an example, the detector 110 may detect a voice signal uttered by a user (or a speaker) using a microphone or the like.

The storage 120 may store an emotion analysis algorithm, an emotional model, user response data for a vehicle sound, and/or the like. The storage 120 may be a non-transitory storage medium which stores instructions executed by the processor 130. The storage 120 may be implemented as at least one of storage media such as a flash memory, a hard disk, a solid state disk (SSD), a secure digital (SD) card, a random access memory (RAM), a static RAM (SRAM), a read only memory (ROM), a programmable ROM (PROM), an electrically erasable and programmable ROM (EEPROM), an erasable and programmable ROM (EPROM), an embedded multimedia card (eMMC) and/or a universal flash storage (UFS).

The processor 130 may obtain user response data (or a sound, an audio, or an utterance) for a vehicle sound such as a virtual sound (e.g., a driving sound, an acceleration sound, and the like) and a warning sound output from an electrification vehicle using the detector 110. The processor 130 may analyze the obtained user response data using the emotion analysis algorithm. The emotion analysis algorithm may encode an utterance of each speaker to derive a result by means of calculation with a target sentence. A conversational memory network (CMN) which is a sound-based text calculation algorithm may be used as the emotion analysis algorithm. The emotion analysis algorithm may serve as a sound-based emotion classifier.

The processor 130 may classify user response data, that is, a user emotion included in a sound, using the sound-based emotion classifier. In other words, the processor 130 may propose an emotion matched with a sound by means of the sound-based emotion classifier.

The processor 130 may convert the classified user emotion, that is, emotion proposal into a concrete attribute (or an emotional attribute). The processor 130 may match emotion proposal with a related keyword. The processor 130 may associate a key word, such as classic music, a game sound, a racing car, or a family voice, with emotion proposal to use hearing experience in the future car.

For example, when a speaker utters that "a quiet and stress-relieving sound will be developed in the future car", the processor 130 may match "a sound like a classic music instrument" as a related keyword. Alternatively, when the speaker utters that "the future car can feel the engine sound when accelerating, making it fun and enjoyable to drive", the processor 130 may match a related keyword, "a sound like a racing game".

The processor 130 may generate an emotional model using an artificial neural network (ANN). The ANN is an algorithm configured to model the human brain and process various data in a similar way to the brain, which has the ability to emotionally analyze and learn a given environment as each neuron serves as a processor which operates independently. When receiving the emotion proposal and the concrete attribute, the ANN may derive an instrumental value by analyzing psychosocial consequences and may use the derived instrumental value to establish an emotional model.

The processor 130 may analyze psychosocial consequences based on the emotional attribute. The processor 130 may classify vehicle environment development needs using a classification technique and may reflect the psychosocial consequences in the classified vehicle environment development needs. At least one of logistic regression (LR), a support vector machine (SVM), or a K-nearest neighbor (KNN) algorithm may be used as the classification technique. The LR may predict a possibility that an emotion score will occur using a linear combination of independent variables. The SVM is one of machine learning fields of artificial intelligence, which may create a non-probability binary linear classification model of determining whether new data will belong to any category based on a dataset given as a supervised learning model for pattern recognition and data analysis. The KNN algorithm may classify new data (or a description variable value) by a majority vote using the result (e.g., a response variable: cluster) of K old data which are most similar (close in distance) to the new data (or the description variable value).

The processor 130 may derive an instrumental value of a sound concept by analyzing psychosocial consequences. The processor 130 may predict a vehicle environment function based on the reflected psychosocial consequences to derive the instrumental value of the sound concept. The processor 130 may derive an instrumental value using at least one of prediction techniques such as multiple linear regression (MLR) or support vector regression (SVR). The MLR may create a regression model for predicting a dependent variable y using several independent variables x. The SVR is a method expanded to solve a regression problem domain based on the excellent predictive ability of the SVM.

The processor 130 may determine a sound concept by means of the classification and the prediction. The sound concept may be classified into three concepts, for example, a cultured sound, an entertaining sound, and an adaptable sound. The cultured sound is soft and luxurious mid-low sound. The entertaining sound is a fun future-oriented sound. The adaptable sound is a sound which changes according to the user's mood. The processor 130 may generate three types of emotional models according to the sound concept. When providing the vehicle sound using the emotional model, the processor 130 may provide three types of warning sounds and virtual sounds based on the emotional model.

Figure 2:
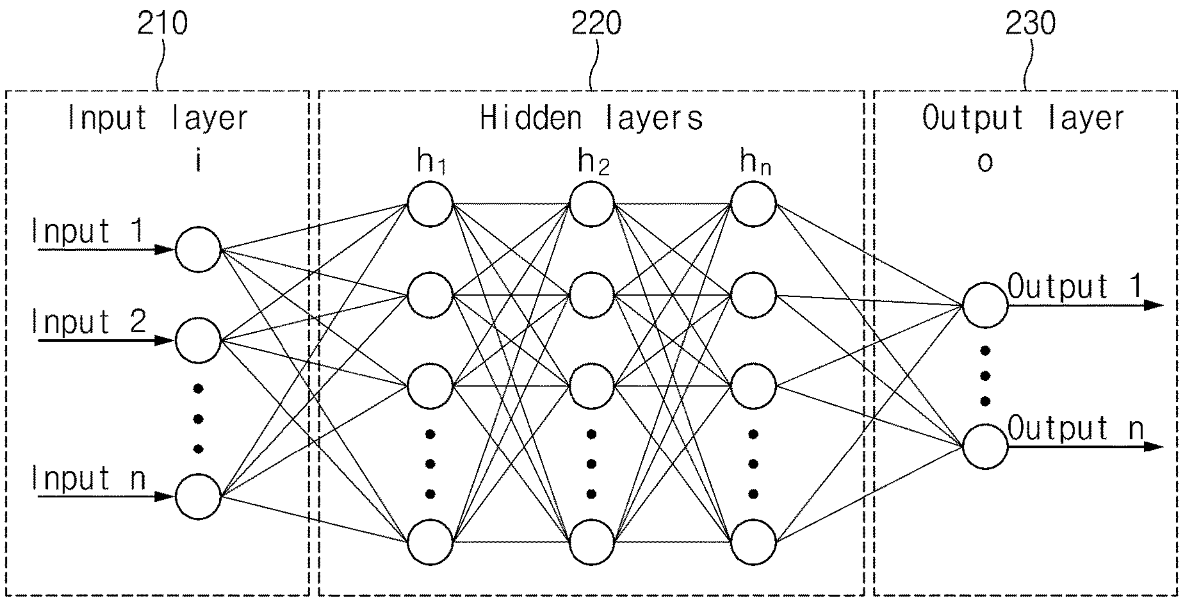
FIG. 2 is a conceptual diagram illustrating an emotion modeling process according to embodiments of the present disclosure.

FIG. 2 is a conceptual diagram illustrating an emotion modeling process according to embodiments of the present disclosure.

A processor 130 of FIG. 1 may perform emotion modeling using an ANN. As shown in FIG. 2, the ANN may be composed of an input layer 210, hidden layers 220, and an output layer 230.

The input layer 210 may analyze a sound detected by sensor(s) (e.g., a voice signal uttered by a user) to derive an emotional state of the user and a concrete attribute (or an emotional attribute). Herein, the sound may be an emotional adjective based on voice interaction of a driver. The emotional adjective may include an emotional text capable of inferring an emotional state and a concrete attribute of which sound you prefer. The input layer 210 may determine an emotional attribute for a sound using an emotion analysis algorithm. The input layer 210 may analyze a sound using a conversational memory network (CMN) and may output an emotional attribute as the analyzed result. The input layer 210 may classify a user emotion (or an emotional state) included in the sound by means of a sound-based emotion classifier. The input layer 210 may convert the classified user emotion into a concrete attribute (or an emotional attribute). The concrete attribute may include a related keyword matched with the classified user emotion. For example, when a driver utters that "Wow that's powerful. When accelerating, the sound is like a speedy and real engine sound. I hope it will be fun and fun to drive like a racing game sound." while the vehicle is traveling, the input layer 210 may analyze an emotional state, a disposition, a preferred sound, and the like of the user by means of an emotional adjective (e.g., powerful, speedy, racing game sound, or fun) included in the uttered voice data to derive a concrete attribute. The input layer 210 may output three provisional classifications of emotion modeling matched with the emotional state of the user and a concrete attribute of each of the three provisional classifications.

The hidden layers 220 may receive the concrete attribute output from the input layer 210 as input data. The hidden layers 220 may reflect psychosocial consequences of a future car by means of classification of vehicle environment development needs using the ANN to create an important value (or an instrumental value) of a sound concept by means of functional prediction of the vehicle environment. The hidden layers 220 may derive an instrumental value of a sound concept by means of the analysis of psychosocial consequences. For example, when the psychosocial consequence of the driver is "stable, natural, and quiet", the hidden layers 220 may derive "being comfortable, safe, and luxurious" as the important value. At this time, the hidden layers 220 may perform emotion modeling using a classification technique algorithm, for example, LR, an SVM, a KNN algorithm, or the like.

The hidden layers 220 may establish a criterion for determining borderline data based on the derived important value and may model three driver emotions based on the established criterion. The hidden layers 220 may receive personalized data through conservative and progress and stability and fun as input data by means of the important value. The hidden layers 220 may establish a criterion for determining three methodologies of the emotion modeling by means of position calculation for conservative and progress on an X-axis and stability and fun on a Y-axis. In other words, the hidden layers 220 may generate three emotional models based on the derived important value (or the derived instrumental value).

The output layer 230 may output the emotional models generated by the hidden layers 220. The output layer 230 may output the emotional models according to the sound concept such as a cultured sound (or a conservative emotion), an entertaining sound (or a future emotion), and an adaptable sound (or a personalized emotion).

Figure 3:
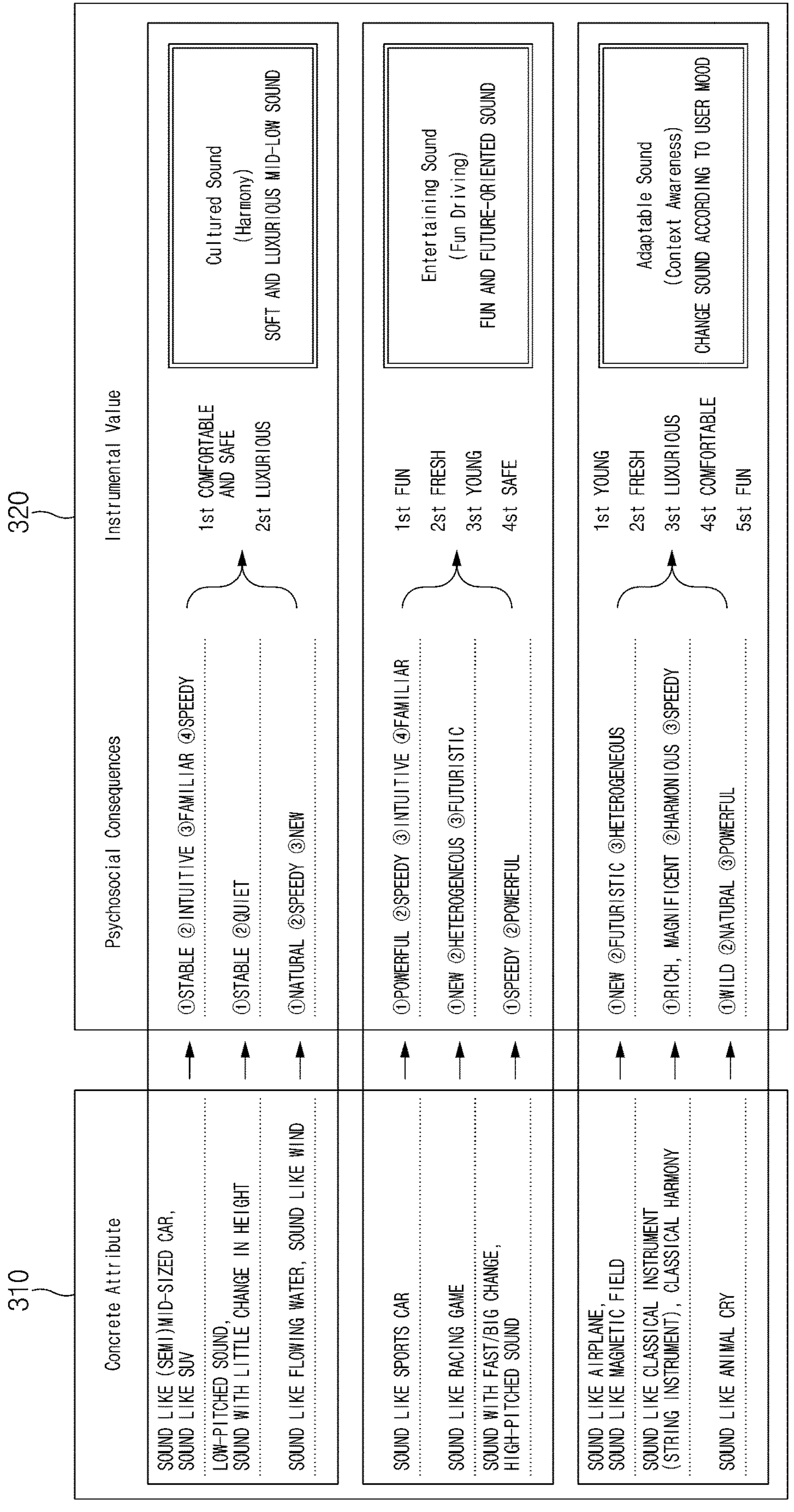
FIG. 3 is a drawing illustrating emotion modeling establishment according to embodiments of the present disclosure.

FIG. 3 is a drawing illustrating emotion modeling establishment according to embodiments of the present disclosure.

Referring to FIG. 3, emotion modeling may be executed by emotion classification logic 310 and model generation logic 320.

The emotion classification logic 310 may determine a sound emotion of a user based on a sound and may output a concrete attribute for the determined sound emotion.

The model generation logic 320 may receive the concrete attribute output from the emotion classification logic 310. The model generation logic 320 may analyze psychosocial consequences based on the concrete attribute. The model generation logic 320 may classify vehicle environment development needs using at least one of classification techniques, such as LR, an SVM, or a KNN algorithm and may reflect psychosocial consequences in the classified vehicle environment development needs.

The model generation logic 320 may derive (or assign) an instrumental value of a sound concept by analyzing the psychosocial consequences. The model generation logic 320 may predict a vehicle environment function using at least one of prediction techniques such as multiple linear regression (MLR) or support vector regression (SVR) to derive the instrumental value of the sound concept. The model generation logic 320 may analyze psychosocial consequences classified based on the concrete attribute to derive the instrumental value.

The model generation logic 320 may generate an emotional model according to the derived instrumental value. As an example, when the instrumental value is "comfortable", "safe", and "luxurious", the model generation logic 320 may generate an emotional model using the concept of a cultured sound. As an example, when the instrumental value is "fun", "fresh", "young", and "safe", the model generation logic 320 may generate an emotional model using the concept of an entertaining sound. As an example, when the instrumental value is "young", "fresh", "luxurious", "comfortable", and "fun", the model generation logic 320 may generate an emotional model using the concept of an adaptable sound.

Figure 4:
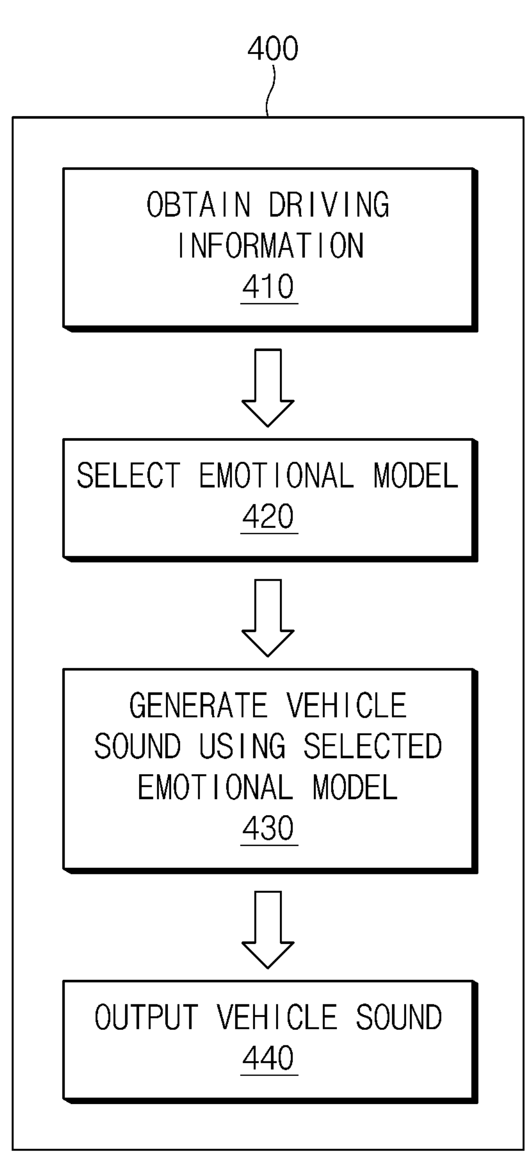
FIG. 4 is a drawing illustrating a process of generating a vehicle sound using an emotional model according to embodiments of the present disclosure.

FIG. 4 is a drawing illustrating a process of generating a vehicle sound using an emotional model according to embodiments of the present disclosure.

A sound generation device 400 may be loaded into an electrification vehicle, such as an electric vehicle (EV), a plug-in hybrid electric vehicle (PHEV), and/or a hybrid electric vehicle (HEY). The sound generation device 400 may generate a vehicle sound, such as a virtual sound (e.g., a driving sound, an acceleration sound, and the like) and a warning sound, using an emotional model generated by an emotion modeling apparatus 100 of FIG. 1. Although not illustrated in the drawing, the sound generation device 400 may include a communication circuit, a memory, at least one processor, and/or the like. The at least one processor may control the overall operation of the sound generation device 400.

In operation 410, the sound generation device 400 may obtain driving information through communication with a sensor and/or an electronic control unit (ECU) in a vehicle. The driving information may include drive mode setting information. The drive mode may be divided into an eco mode, a comfort mode, a sports mode, a smart mode.

In operation 420, the sound generation device 400 may select an emotional model based on the driving information. The sound generation device 400 may determine an emotional model based on a drive mode setting.

In operation 430, the sound generation device 400 may generate a vehicle sound using the selected emotional model. The sound generation device 400 may generate a vehicle sound in connection with the selected emotional model. For example, when the drive mode is set to the eco mode, the sound generation device 400 may turn off the vehicle sound. When the drive mode is set to the comfort mode, the sound generation device 400 may generate a vehicle sound (or an emotional sound) of the concept of a cultured sound. Alternatively, when the drive mode is set to the sports mode, the sound generation device 400 may generate a vehicle sound depending on the concept of an entertaining sound linked to the set sports mode. When the drive mode is set to the smart mode, the sound generation device 400 may generate a vehicle sound depending on the concept of an adaptable sound linked to the smart mode.

In operation 440, the sound generation device 400 may play and output the generated vehicle sound. The sound generation device 400 may output the played vehicle sound through a speaker.

According to an exemplary embodiment of the present disclosure, by applying a different emotional model depending on the drive mode set by a driver, the sound generation device 400 may provide three types of vehicle sounds, that is, a virtual sound and a warning sound, based on the emotional model.

Figure 5:
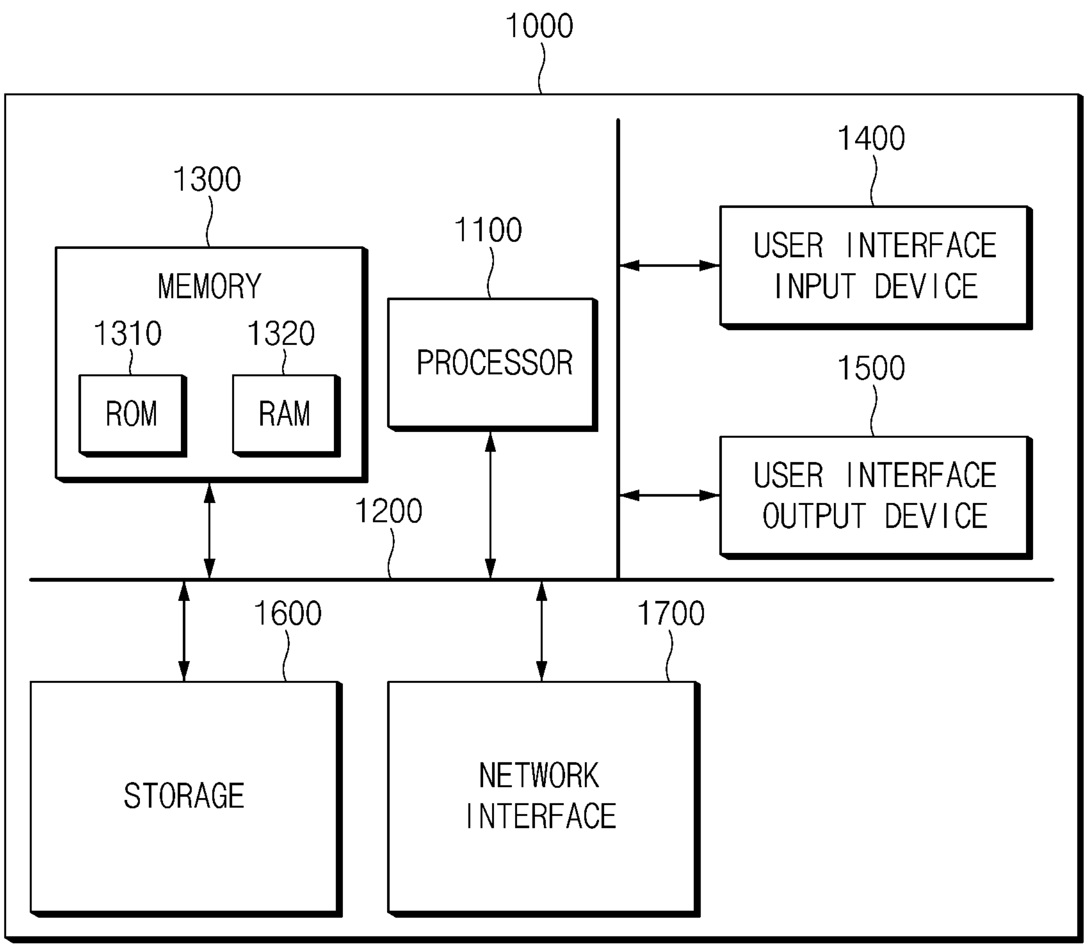
FIG. 5 is a block diagram illustrating a computing system for executing an emotion modeling method according to embodiments of the present disclosure.

FIG. 5 is a block diagram illustrating a computing system for executing an emotion modeling method according to embodiments of the present disclosure.

Referring to FIG. 5, a computing system 1000 may include at least one processor 1100, a memory 1300, a user interface input device 1400, a user interface output device 1500, storage 1600, and a network interface 1700, which are connected with each other via a bus 1200.

The processor 1100 may be a central processing unit (CPU) or a semiconductor device that processes instructions stored in the memory 1300 and/or the storage 1600. The memory 1300 and the storage 1600 may include various types of volatile or non-volatile storage media. For example, the memory 1300 may include a read only memory (ROM) 1310 and a random access memory (RAM) 1320.

Thus, the operations of the method or the algorithm described in connection with the embodiments disclosed herein may be embodied directly in hardware or a software module executed by the processor 1100, or in a combination thereof. The software module may reside on a storage medium (that is, the memory 1300 and/or the storage 1600) such as a RAM, a flash memory, a ROM, an EPROM, an EEPROM, a register, a hard disk, a removable disk, and a CD-ROM. The exemplary storage medium may be coupled to the processor 1100. The processor 1100 may read out information from the storage medium and may write information in the storage medium. Alternatively, the storage medium may be integrated with the processor 1100. The processor 1100 and the storage medium may reside in an application specific integrated circuit (ASIC). The ASIC may reside within a user terminal. In another case, the processor 1100 and the storage medium may reside in the user terminal as separate components.

According to embodiments of the present disclosure, the emotion modeling apparatus may provide a customized vehicle sound with regard to an emotion of the user in a vehicle environment.

Hereinabove, although the present disclosure has been described with reference to exemplary embodiments and the accompanying drawings, the present disclosure is not limited thereto, but may be variously modified and altered by those skilled in the art to which the present disclosure pertains without departing from the spirit and scope of the present disclosure claimed in the following claims. Therefore, embodiments of the present disclosure are not intended to limit the technical spirit of the present disclosure but provided only for the illustrative purpose. The scope of the present disclosure should be construed on the basis of the accompanying claims, and all the technical ideas within the scope equivalent to the claims should be included in the scope of the present disclosure.

What is claimed is:

1. An emotion modeling method, comprising:

receiving a sound uttered by a user comprising an emotional adjective;

determining an emotional attribute based on the sound using an emotion analysis algorithm comprising a conversational memory network (CMN) by analyzing the emotional adjective to derive a disposition and a preferred sound of the user;

deriving an instrumental value of a sound concept by:

classifying vehicle environment development needs using at least one of logistic regression (LR) a support vector machine (SVM), or a K-nearest neighbor (KNN) algorithm;

reflecting psychosocial consequences in the classified vehicle environment development needs; and predicting a vehicle environment function using at least one of multiple linear regression (MLR) or support vector regression (SVR) to derive the instrumental value by analyzing psychosocial consequences of the emotional attribute using an artificial neural network;

generating a plurality of emotional models based on the instrumental value of the sound concept, wherein the plurality of emotional models comprise a cultured sound model, an entertaining sound model, and an adaptable sound model;

selecting one of the plurality of emotional models based on a drive mode, wherein the drive mode is one of an eco mode, a comfort mode, a sports mode, and a smart mode and wherein:

when the drive mode is set to the comfort mode, the cultured sound model is selected;

when the drive mode is set to the sports mode, the entertaining sound model is selected; and when the drive mode is set to the smart mode, the adaptable sound model is selected;

generating a vehicle sound corresponding to the selected emotional model using the selected emotional model; and outputting the generated vehicle sound through a speaker, wherein, when the drive mode is set to the eco mode, the vehicle sound is turned off;

wherein the generating of the emotional model comprises:

establishing a criterion of determining borderline data by performing position calculation of conservative and progress and stability and fun by receiving personalized data as input data using the derived instrumental value of the sound concept; and determining an emotion modeling methodology based on the criterion; and wherein establishing the criterion of determining borderline data comprises establishing the criterion for determining three methodologies of the emotion modeling using the position calculation for conservative and progress on an X-axis and stability and fun on a Y-axis to be used in generating the plurality of emotional models.

2. The emotion modeling method of claim 1, wherein the determining of the emotional attribute comprises:

classifying a user emotion included in the sound using an emotion classifier; and converting the classified user emotion into a concrete attribute.

3. The emotion modeling method of claim 2, wherein the converting of the classified user emotion into the concrete attribute comprises:

matching a related keyword with the classified user emotion.

4. An emotion modeling apparatus, comprising:

a detector configured to detect a sound uttered by a user comprising an emotional adjective; and a processor configured to:

determine an emotional attribute based on the sound using an emotion analysis algorithm comprising a conversational memory network (CMN) by analyzing the emotional adjective to derive an emotional state, a disposition and a preferred sound of the user, derive an instrumental value of a sound concept by:

classifying vehicle environment development needs using at least one of logistic regression (LR), a support vector machine (SVM), or a K-nearest neighbor (KNN) algorithm;

reflecting psychosocial consequences in the classified vehicle environment development needs; and predicting a vehicle environment function using at least one of multiple linear regression (MLR) or support vector regression (SVR) to derive the instrumental value by analyzing psychosocial consequences of the emotional attribute using an artificial neural network, generate a plurality of emotional models based on the instrumental value of the sound concept, wherein the plurality of emotional models comprise a cultured sound model, an entertaining sound model, and an adaptable sound model;

select one of the plurality of emotional models based on a drive mode, wherein the drive mode is one of an eco mode, a comfort mode, a sports mode, and a smart mode and wherein:

when the drive mode is set to the comfort mode, the cultured sound model is selected;

when the drive mode is set to the sports mode, the entertaining sound model is selected; and when the drive mode is set to the smart mode, the adaptable sound model is selected;

generate a vehicle sound corresponding to the selected emotional model using the selected emotional model; and output the generated vehicle sound through a speaker, wherein, when the drive mode is set to the eco mode, the vehicle sound is turned off;

wherein the processor is further configured to:

establish a criterion of determining borderline data by performing position calculation of conservative and progress and stability and fun by receiving personalized data as input data using the derived instrumental value of the sound concept, and determine an emotion modeling methodology based on the criterion;

wherein establishing the criterion of determining borderline data comprises determining three methodologies of the emotion modeling using position calculation for conservative and progress on an X-axis and stability and fun on a Y-axis to be used in generating the plurality of emotional models.

5. The emotion modeling apparatus of claim 4, wherein the processor is further configured to:

classify a user emotion included in the sound using an emotion classifier, and convert the classified user emotion into a concrete attribute.

6. The emotion modeling apparatus of claim 5, wherein the processor is further configured to match a related keyword with the classified user emotion.

* * * * *